United States Patent
Eisele et al.

(10) Patent No.: US 9,339,324 B2
(45) Date of Patent: May 17, 2016

(54) RADIO FREQUENCY SURGICAL APPARATUS

(75) Inventors: Florian Eisele, Freiburg (DE); Heiko Schall, Nurtingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 994 days.

(21) Appl. No.: 13/148,089

(22) PCT Filed: Jan. 25, 2010

(86) PCT No.: PCT/EP2010/000419
§ 371 (c)(1),
(2), (4) Date: Sep. 2, 2011

(87) PCT Pub. No.: WO2010/089037
PCT Pub. Date: Aug. 12, 2010

(65) Prior Publication Data
US 2011/0306960 A1    Dec. 15, 2011

(30) Foreign Application Priority Data

Feb. 6, 2009   (DE) .......................... 10 2009 007 861
Mar. 9, 2009   (DE) .......................... 10 2009 012 387

(51) Int. Cl.
*A61B 18/18*   (2006.01)
*A61B 18/12*   (2006.01)
*A61B 18/04*   (2006.01)

(52) U.S. Cl.
CPC ..... *A61B 18/1206* (2013.01); *A61B 2018/1273* (2013.01)

(58) Field of Classification Search
CPC ... A61N 1/08; A61N 1/3962; A61N 1/37235; A61N 1/36125; A61N 1/36014; A61N 1/37211; A61N 1/378; A61N 1/36128; A61N 1/3975; A61B 5/04288; A61B 18/12; H01R 13/66; H01R 43/26; H04W 52/0274; H04W 56/00
USPC ...................... 600/26–28; 606/31–42; 607/60
See application file for complete search history.

(56) References Cited

U.S. PATENT DOCUMENTS

2006/0200120 A1   9/2006   DiCarlo et al.
2007/0255269 A1   11/2007  Shin
2008/0009850 A1   1/2008   Goble et al.

FOREIGN PATENT DOCUMENTS

CN           101061968 A       10/2007

(Continued)

*Primary Examiner* — Joseph Stoklosa
*Assistant Examiner* — Brian M Antiskay
(74) *Attorney, Agent, or Firm* — Blank Rome LLP

(57) ABSTRACT

An RF surgical apparatus and method for operating such an apparatus. The RF surgical apparatus comprises at least two RF generators and at least one neutral electrode output for one neutral electrode. At least two outputs for connecting RF surgical instruments for applying treatment currents to the surgical instruments are provided. Furthermore, a switching device is provided. To enable a simultaneous operation of several RF surgical apparatuses, and not generate any neuromuscular stimulation, a separate generator is provided for each RF surgical instrument and a single neutral electrode is provided for all of the instruments and generators. The switching device is adapted to be arranged in a controlling connection with the RF generators such that the RF generators will never generate, and output to the instruments, any treatment currents at the same time (that is, they output only sequentially).

12 Claims, 3 Drawing Sheets

(56) References Cited

FOREIGN PATENT DOCUMENTS

| CN | 101072543 A | 11/2007 |
| DE | 699 21 963 T2 | 12/2005 |
| DE | 10 2005 007 769 A1 | 8/2006 |
| EP | 1 112 720 A1 | 7/2001 |
| JP | 2006-519080 A | 8/2006 |
| WO | WO 01/12089 A1 | 2/2001 |
| WO | WO 2004/078050 A2 | 9/2004 |
| WO | WO 2005/117735 A1 | 12/2005 |

RADIO FREQUENCY SURGICAL APPARATUS

FIELD OF THE INVENTION

Embodiments of the invention relate to an RF surgical apparatus comprising at least two RF generators.

BACKGROUND

A vast number of RF surgical apparatuses have been known. In general, these apparatuses comprise an RF generator and a surgical instrument. Many RF surgical instruments are designed as so-called monopolar instruments, in which a large-surface neutral electrode is attached with good contact to the body (mostly the thigh) of the patient so that the actual treatment current from a treatment electrode flows through the body of the patient and through the neutral electrode for coagulation, cutting, etc. by an RF surgical technique.

In some surgeries, it is desirable for several surgeons to work on the same patient with RF surgical instruments at the same time. From publication DE 10 2005 007 769 A1, an RF surgical apparatus enabling the connection of several instruments—via one switch, respectively—to a single output of a single RF generator is known. Indeed, such an RF surgical apparatus allows simultaneous surgeries; however, at all times, the instruments can only be driven in the same operating mode that has been prespecified by the RF generator. Furthermore, considering the known arrangement, there is a problem that the instruments or active electrodes are connected in parallel, via relays, to the output of the RF generator. If two surgeons operate at the same time, the generator feeds two active electrodes in a parallel manner. The power output by the generator, however, is divided in a non-uniform manner that is consistent with the tissue properties on the active electrodes. A control of the adjusted currents, as is common in RF generators, can no longer be performed in this manner.

Now, to ensure that two instruments will be able to work with different adjustments of the RF generator, it is conceivable to drive two completely independent RF surgical devices with one dedicated active electrode and one dedicated neutral electrode. Indeed, in this case, completely independent output and operating mode adjustments can be implemented; however, if the arrangement of the neutral electrode is unfavorable, in particular if one body region is perfused by both RF currents at the same time, neuromuscular stimulations due to floating currents can occur. For this reason, this procedure is viewed as being dangerous.

SUMMARY

It is the object of the embodiments of the invention to develop an RF surgical apparatus of the aforementioned type in which the surgical instruments can still be operated in different modes while neuromuscular stimulation is prevented.

This object is achieved by an RF surgical apparatus comprising at least two RF generators, at least one neutral electrode output for a neutral electrode, at least two outputs for connecting RF surgical instruments for the application of treatment currents to the RF surgical instruments, and a switching device. In doing so, a separate RF generator is provided for each RF surgical instrument, and a single neutral electrode arrangement is provided for all of the instruments and the RF generators, respectively. The switching device is adapted to be arranged in a controlling connection with the RF generators such that the RF generators will never generate, and output to the instruments, treatment currents at the same time, i.e., they will only do so sequentially.

Consequently, in accordance with the embodiments of invention, two different RF surgical generators are provided, whereby each generator can be switched into an operating mode that is appropriate for the RF surgical instrument that is to be used. It is also possible to perform control operations because each generator is operated individually or alone, even though at all times they are operated for a short time only.

The switching device may be provided as a separate unit. Preferably, the switching device comprises a controller or a master generator that controls the other RF generators as slave generators via SYNC pulses or similarly controlling pulses. In this manner, the entire RF surgical apparatus may be constructed in a compact manner. In particular, in doing so, the master generator must comprise one of the aforementioned RF generators.

Preferably, the switching device is configured such that the number of RF generators connected therewith is determined and their control is consistent with the determined number in a uniform sequence. In this manner, it is possible for the surgical team to work with one, two or more RF generators (and RF surgical instruments), without separate manual adjustment of the equipment.

The switching device and the RF generators comprise communication interfaces, for example, a field bus, and are configured such that the RF generators receive defined start times, at which the RF generators generate a treatment current, and/or time slots ($T_{On\ \frac{1}{2}}$), during which the RF generators generate a treatment current. Preferably, these time slots are adjusted such that sufficient duration is available for each RF generator so that the respective RF generator emits, and is also able to control, a signal that is effective in the treatment technique.

Preferably, the switching device is configured such that there are pauses between the discharges of treatment currents by the RF generators. This ensures that the circuits are capable of settling, i.e., that there will be no residual currents of a current discharge operation at the start of a subsequent current discharge operation. The advantages of this process have already been previously described.

Preferably, the clock frequency is 10 kHz to 100 kHz. In this way, it is ensured that quasi-continuous surgery can be performed without the surgeon noticing a substantial difference compared to working with a single RF generator (and the connected single RF surgical instrument). It should be appreciated that the operation of several generators and RF surgical instruments is still possible.

BRIEF DESCRIPTION OF THE DRAWINGS

Embodiments of the invention will be described in greater detail with reference to the drawings, in which.

DETAILED DESCRIPTION

In the following description, the same reference signs are used for the same components or for components that have the same function.

Figure 1:
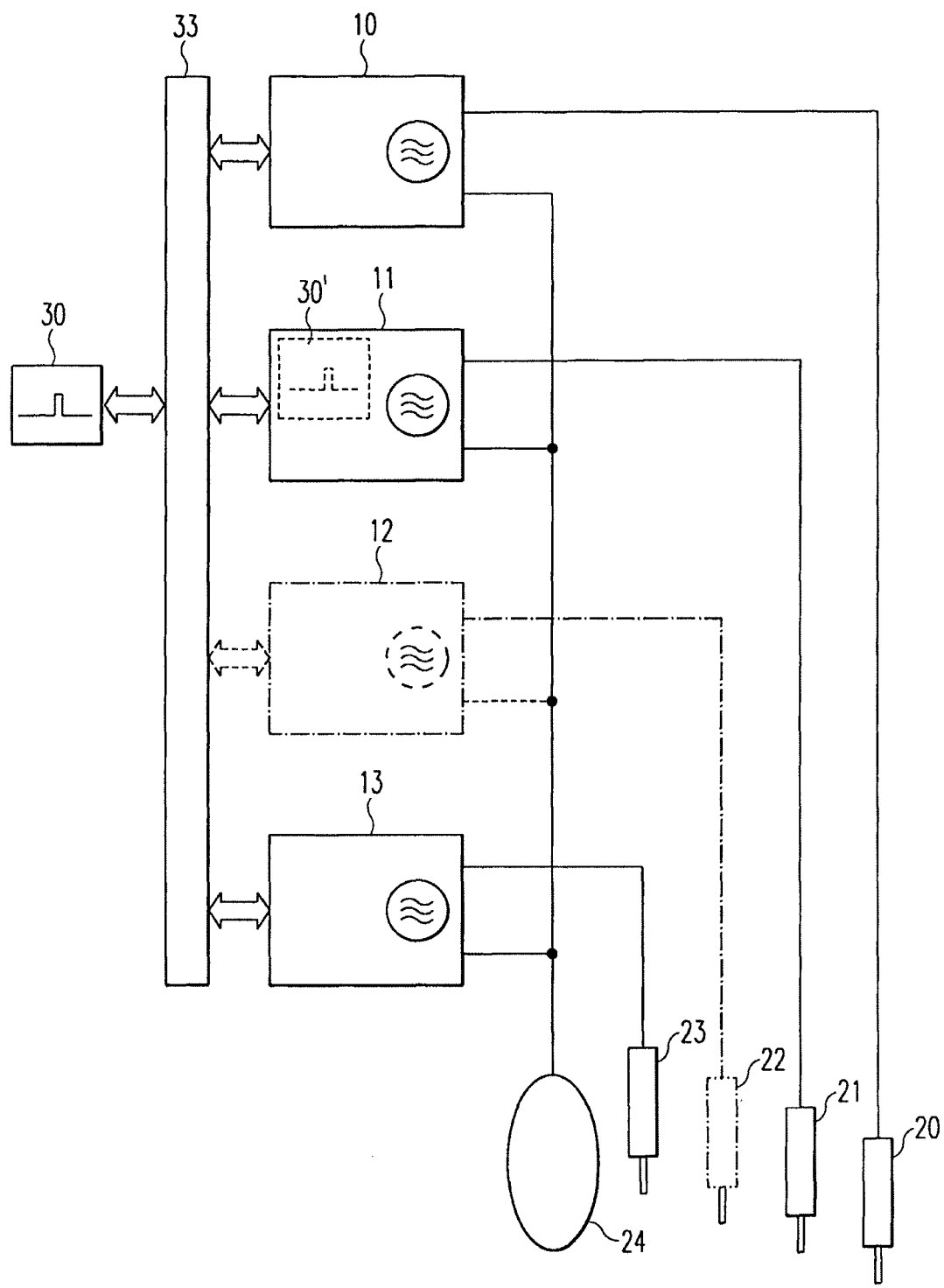
FIG. 1 is a highly schematic circuit diagram of an embodiment of the RF surgical apparatus in accordance with the disclosed embodiments of the invention.

In accordance with FIG. 1, the apparatus is provided with a plurality of RF generators 10, 11, 12, 13. The outputs of these RF generators 10-13, which in the normal situation are connected to one neutral electrode, are now interconnected and connected to a single neutral electrode 24. The additional outputs of the RF generators 10-13 are respectively connected to RF surgical instruments 20, 21, 22, 23 (said instruments being indicated only in a highly schematical manner). In FIG. 1, the dotted lines of RF generator 12 and its associated RF surgical instrument 22 are intended to indicate that the number of RF generators is essentially as desired. That is, the embodiment is not limited to the number of RF generators and RF surgical instruments.

All of the RF generators 10-13 are connected to each other via a shared bus 33 and one switching device 30. This switching device 30 may also be located in one of the generators such as the switching device 30' illustrated e.g., in RF generator 11. The bus 33 has, in particular, the function of synchronizing the RF generators that, as is known, can be controlled such that they can activate and deactivate their RF signals (typically 300 kHz to 4 MHz) within extremely short times.

Figure 2:
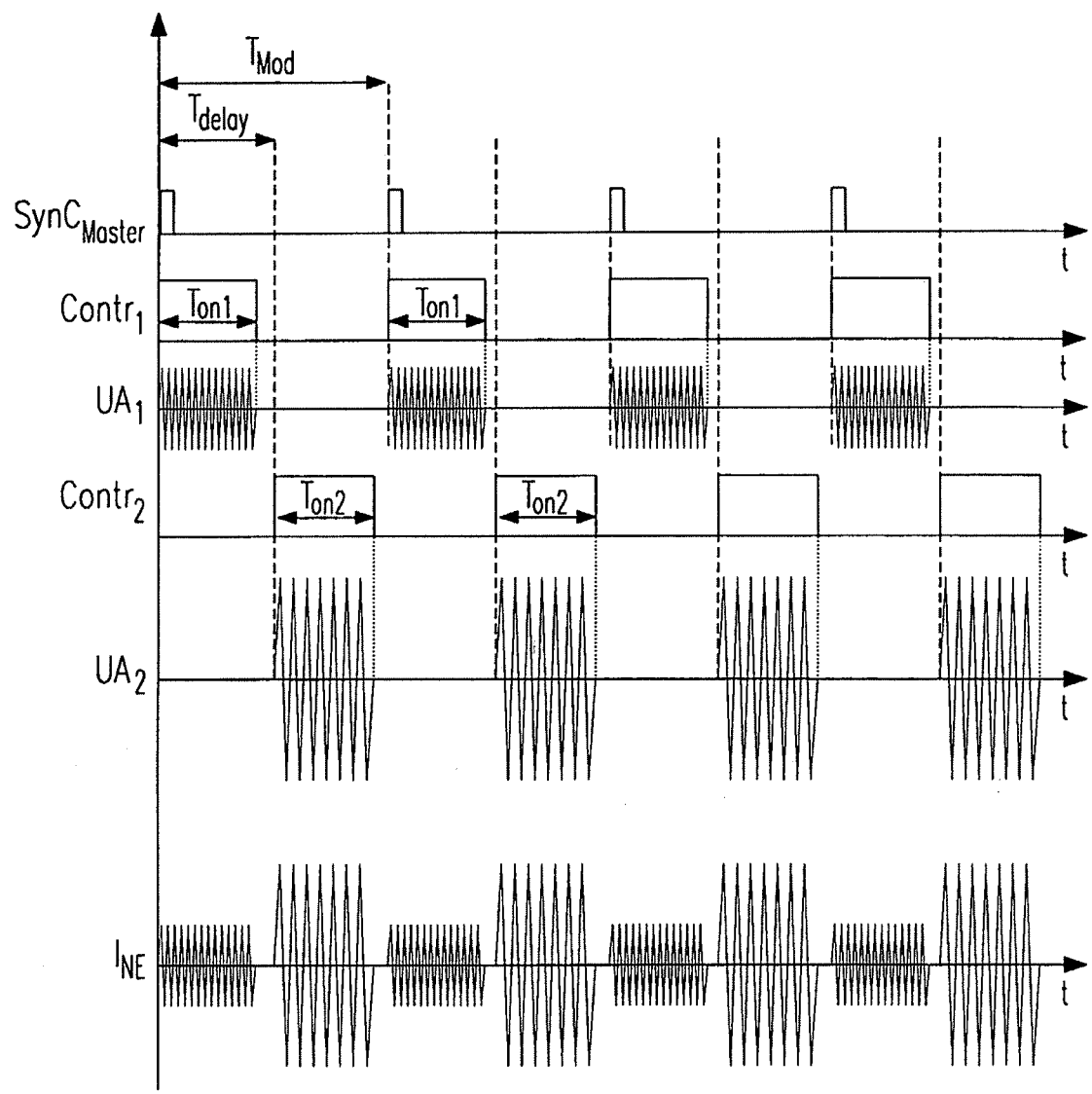
FIG. 2 illustrates a first option for controlling two RF surgical generators with the use of output signals.

FIG. 2 is a time-dependency diagram that shows only two RF generators. The switching device 30 (or 30') emits a $SYNC_{Master}$ pulse sequence that is repeated with a cycle duration $T_{mod}$. In addition, the switching device (30, 30') outputs a delay time $T_{delay}$ and activation times $T_{On1}$ and $T_{On2}$ to the second connected generator.

As a result, following each $SYNC_{Master}$, a control signal Contr is emitted, said control signal Contr activating the first RF generator 10 such that said generator emits an output signal $UA_1$ for the time $T_{On1}$. Following the delay time $T_{delay}$, a second control signal $Contr_2$ is generated, during which ($T_{On2}$) the second generator emits an output signal $UA_2$. As a result, current $I_{NE}$ flows through the neutral electrode, said current being shown in FIG. 2 in the bottom-most diagram and being composed of the two partial currents $UA_1$ and $UA_2$. As a rule, t $T_{delay}$ is greater than $T_{On1}$, and $T_{delay}$ $T_{On2}$ is less than $T_{Mod}$.

FIG. 2 also shows that the periods of time are selected such that each of the outputs $UA_1$ and $UA_2$ has settled before the next output rises again.

In this manner, respective "slices of time" $T_{On1}$ and $T_{On2}$ are allocated to the two generators within the modulation, said slices of time being time-synchronized via the $SYNC_{Master}$ signal. The slices of time must not overlap to avoid floating currents—and thus neuromuscular stimulations—in the current through the shared neutral electrode.

Both generators may be operated in different modes and with different power settings because they can be controlled and actuated independently of each other.

Of course, there are restrictions in view of the operating mode selection. For example, continuous generator modes without modulation are not enabled. The sum of the relative durations of actuation (duty cycle) must be less than 1, wherein the relative duration of actuation τ is defined as:

$$\tau_{1/2} = \frac{T_{On1,2}}{T_{Mod}}$$

Figure 3:
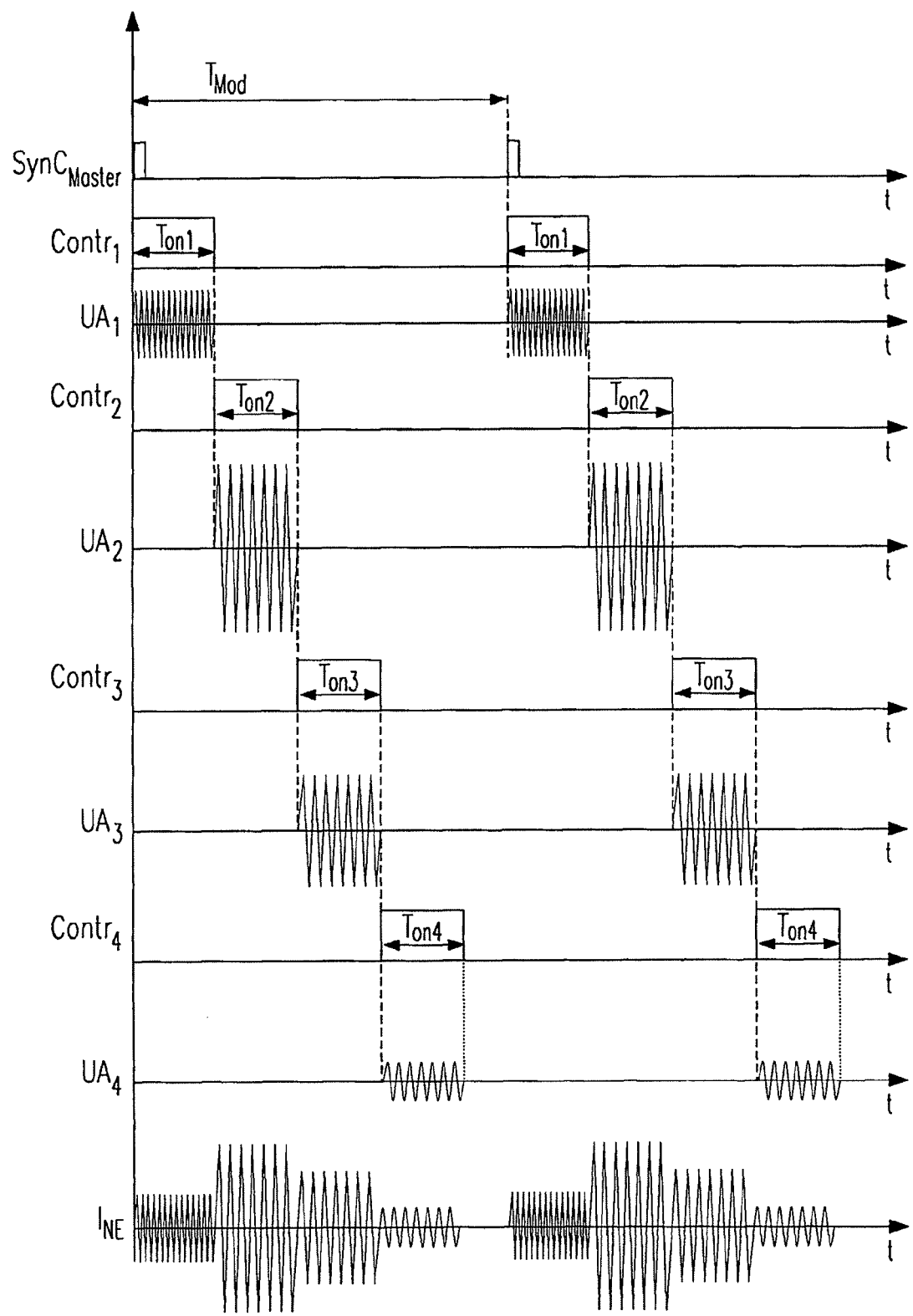
FIG. 3 illustrates a second embodiment for controlling several RF surgical generators.

Referring to the operating mode shown in FIG. 3, the $SYNC_{Master}$ pulse only controls the first generator such that it outputs a signal during its operating time $T_{On1}$. The second RF generator is actuated to only emit an output signal $UA_2$ after the activation time $T_{On1}$ of the first generator has passed. The third generator is activated in the same manner by the second generator, and, thereafter, the fourth generator is activated in the same manner by the third generator. It is only then that an actuation by the $SYNC_{Master}$ pulse will occur again after the cycle duration $T_{Mod}$. The resultant current $I_{NE}$ through the neutral electrode is indicated at the very bottom of FIG. 3. The essential difference between the FIG. 3 embodiment and that of FIG. 2 is that the RF generators are successively activated in a chain-like manner with only the first generator being activated by a superimposed pulse sequence.

Thus, it has been shown that the method of alternately activating the RF generators in accordance with the embodiments of the invention can be implemented in different ways.

The invention claimed is:

1. An RF surgical apparatus comprising:
    at least two RF generators connected to each other by a shared bus;
    at least one neutral electrode output for a neutral electrode;
    at least two outputs for connecting RF surgical instruments for applying treatment currents to the surgical instruments; and
    a switching device coupled to the shared bus and arranged in a controlling connection with the RF generators via the shared bus such that the RF generators do not generate, and output to the RF surgical instruments, treatment currents at the same time,
    wherein the shared bus is configured to synchronize the at least two RF generators to allow the at least two RF generators to activate and deactivate respective signals.

2. The RF surgical apparatus of claim 1, wherein the switching device comprises a controller that controls the RF generators via controlling pulses.

3. The RF surgical apparatus of claim 2, wherein the controlling pulses are SYNC pulses.

4. The RF surgical apparatus of claim 1, wherein the switching device comprises a master generator that controls remaining RF generators as slave generators via controlling pulses.

5. The RF surgical apparatus of claim 4, wherein the controlling pulses are SYNC pulses.

6. The RF surgical apparatus of claim 4, wherein the master generator comprises one of the at least two RF generators.

7. The RF surgical apparatus of claim 1, wherein the switching device is connected to a determined number of RF generators and the switching device is configured to control the determined number of RF generators in a determined sequence.

8. The RF surgical apparatus of claim 1, wherein the switching device and the RF generators comprise communication interfaces and are configured such that the RF generators receive defined start times at which the RF generators generate a treatment current.

9. The RF surgical apparatus of claim 8, wherein the communication interfaces comprise the shared bus.

10. The RF surgical apparatus of claim 1, wherein the switching device and the RF generators comprise communication interfaces and are configured such that the RF generators receive defined time slots at which the RF generators generate a treatment current.

11. The RF surgical apparatus of claim 1, wherein the switching device is configured such that there are pauses between discharges of treatment currents by the RF generators.

12. The RF surgical apparatus of claim 1, wherein a separate RF generator is provided for each RF surgical instrument, and a single neutral electrode output is provided for all of the RF surgical instruments and generators.

* * * * *